(12) United States Patent
Isono et al.

(10) Patent No.: US 11,458,088 B2
(45) Date of Patent: Oct. 4, 2022

(54) COSMETIC MOLDED ARTICLE AND METHOD FOR MANUFACTURING SAME

(71) Applicant: DAINICHISEIKA COLOR & CHEMICALS MFG. CO., LTD., Tokyo (JP)

(72) Inventors: Yasuyuki Isono, Tokyo (JP); Yu Aso, Tokyo (JP)

(73) Assignee: Dainichiseika Color & Chemicals Mfg. Co., Ltd., Tokyo (JP)

( * ) Notice: Subject to any disclaimer, the term of this patent is extended or adjusted under 35 U.S.C. 154(b) by 191 days.

(21) Appl. No.: 16/755,800

(22) PCT Filed: Oct. 24, 2018

(86) PCT No.: PCT/JP2018/039464
§ 371 (c)(1),
(2) Date: Apr. 13, 2020

(87) PCT Pub. No.: WO2019/082922
PCT Pub. Date: May 2, 2019

(65) Prior Publication Data
US 2021/0186847 A1    Jun. 24, 2021

(30) Foreign Application Priority Data

Oct. 27, 2017 (JP) .............................. JP2017-208270

(51) Int. Cl.
| | | |
|---|---|---|
| A61K 8/73 | (2006.01) | |
| A61K 8/02 | (2006.01) | |
| A61Q 19/00 | (2006.01) | |
| A61Q 19/08 | (2006.01) | |

(52) U.S. Cl.
CPC ............ *A61K 8/735* (2013.01); *A61K 8/0216* (2013.01); *A61Q 19/007* (2013.01); *A61Q 19/08* (2013.01)

(58) Field of Classification Search
CPC ................................ A61K 8/735; A61K 8/026
See application file for complete search history.

(56) References Cited

U.S. PATENT DOCUMENTS

| | | | |
|---|---|---|---|
| 7,998,379 B2 * | 8/2011 | Malessa ................... | A61L 15/28 264/49 |
| 2016/0208064 A1 * | 7/2016 | Isono ..................... | A61L 31/042 |
| 2016/0333119 A1 | 11/2016 | Yamazaki et al. | |
| 2018/0021477 A1 | 1/2018 | Isono et al. | |

FOREIGN PATENT DOCUMENTS

| | | |
|---|---|---|
| EP | 1005874 | 6/2000 |
| EP | 3103815 | 12/2016 |
| JP | 63-159452 | 7/1988 |
| JP | 03-063209 | 3/1999 |
| JP | 2000-229837 | 8/2000 |
| JP | 2010-043022 | 2/2010 |
| JP | 2013-181001 | 9/2013 |
| JP | 2017-025157 | 2/2017 |
| JP | 2017-048306 | 3/2017 |
| JP | 2018-177643 | 11/2018 |
| KR | 10-2015-0025432 | 3/2015 |
| NO | 95/18635 | 7/1995 |
| WO | 2014/061332 | 4/2014 |
| WO | 2015/108029 | 7/2015 |
| WO | 2016/136884 | 9/2016 |

OTHER PUBLICATIONS

Kewpie Corporation, Fine chemical Division, last modified on Aug. 18, 2017.*
Second Japanese Office Action, issued in the corresponding Japanese patent application No. 2017-208270, dated Mar. 2, 2021, 9 pages (machine translation enclosed).
Extended European Search Report, issued in corresponding European Patent Application No. 18869817.9, dated Jul. 15, 2021, 11 pages.
Japanese Office Action, issued in corresponding Japanese Patent Application No. 2017-208270, dated Jun. 23, 2020, 8 pages including English translation.
International Preliminary Report on Patentability, issued in corresponding PCT Application No. PCT/JP2018/039464, dated Apr. 28, 2020, 16 pages.
International Search Report, issued in the corresponding PCT application No. PCT/JP2018/039464, dated Jan. 15, 2019, 5 pages.
Korean Office Action, issued in the corresponding Korean Patent Application No. 10-2020-7010295, dated Jan. 10, 2022, 8 pages (including translation).

* cited by examiner

*Primary Examiner* — Gina C Justice
(74) *Attorney, Agent, or Firm* — Hamre, Schumann, Mueller & Larson, P. C.

(57) ABSTRACT

The present invention provides a cosmetic shaped product: which is substantially formed with relatively low-molecular-weight hyaluronic acid or a water-soluble salt thereof having a high penetrability into the skin; which is easily soluble to water; and which has satisfactory handling properties, and a method for producing the cosmetic shaped product. There is provided a cosmetic shaped product being a sponge-like shaped body formed with at least one polyanionic polysaccharide of hyaluronic acid and a water-soluble salt thereof each having an average molecular weight of 30,000 or lower, the sponge-like shaped body having a bulk specific gravity of 5 to 500 mg/mL. This cosmetic shaped product can be produced by freeze-drying an aqueous solution having a content of the polyanionic polysaccharide of 0.5 to 30% by mass.

3 Claims, 2 Drawing Sheets

[Figure 1]
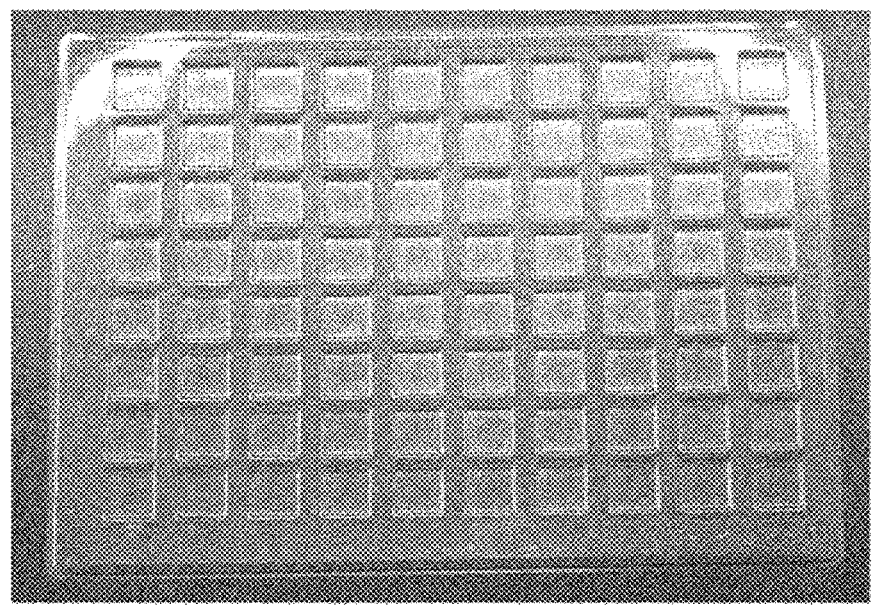
[Figure 2]
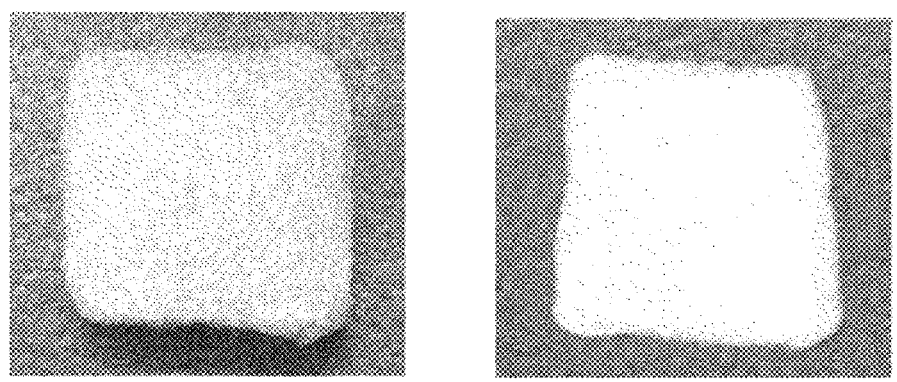

[Figure 3]
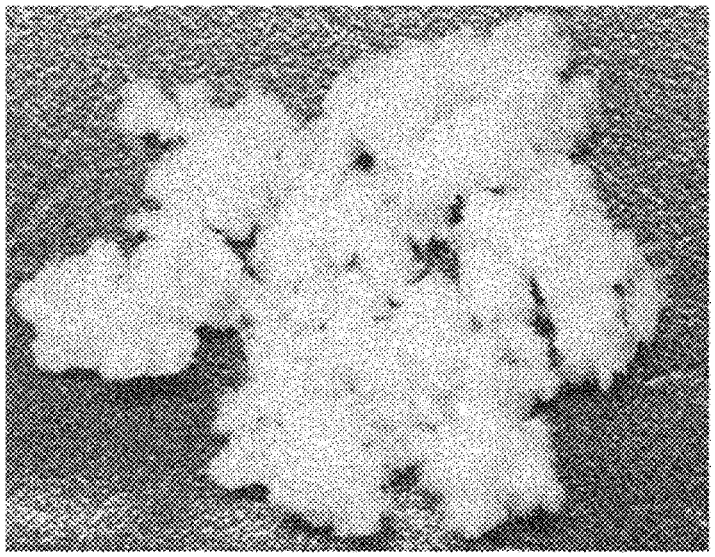
[Figure 4]

COSMETIC MOLDED ARTICLE AND METHOD FOR MANUFACTURING SAME

TECHNICAL FIELD

The present invention relates to: a cosmetic shaped product that is easily soluble to water and is excellent in penetrability of hyaluronic acid, which is an active ingredient, into the skin; and a method for producing the cosmetic shaped product.

BACKGROUND ART

Hyaluronic acid, which is a kind of polyanionic polysaccharides, and a water-soluble salt thereof (hereinafter, also simply written as "hyaluronic acid") are excellent in physical properties, such as water-retaining properties, viscosity, and tackiness. Further, hyaluronic acid and a water-soluble salt thereof exhibit a high degree of safety and of biocompatibility and are therefore each widely used as a raw material for medical materials, food materials, cosmetic materials, and the like. For example, in the medical field, hyaluronic acid and a water-soluble salt thereof are each utilized as a material for a joint lubricant or an antiadhesive material. In addition, in the cosmetic field, hyaluronic acid and a water-soluble salt thereof are each utilized as a material for cosmetics making use of an ameliorating effect on a rough skin, an ameliorating effect on keratin, and a moisture-retaining effect.

Further, a film-like shaped body (film or sheet) mainly containing hyaluronic acid is widely used for applications such as a face mask or pack agent for make-up, a medical patch, and an antiadhesive material from the viewpoints of adhesiveness, coverability, a protecting effect, and the like. For example, a sheet-like hyaluronic acid gel to be used as a cosmetic, the sheet-like hyaluronic acid gel containing hyaluronic acid having a molecular weight of 50000 to 5000000, is proposed (Patent Literature 1). Moreover, a film composition to be used as a cosmetic pack agent or the like, the film composition containing as a main component hyaluronic acid having a molecular weight of 10000 or higher, is proposed (Patent Literature 2).

CITATION LIST

Patent Literature

Patent Literature 1: International Publication No. WO2014061332
Patent Literature 2: Japanese Patent Laid-Open No. 63-159452

SUMMARY OF INVENTION

Technical Problem

It is known that hyaluronic acid has different action mechanisms depending on the molecular weight thereof. For example, high-molecular-weight hyaluronic acid can cover a treatment part in the form of a film coat and therefore exhibits efficacy such as protection, moisture retention, and amelioration of rough skin. On the other hand, low-molecular-weight hyaluronic acid is a component that easily penetrates into the skin and therefore is known to activate skin cells and exhibit efficacy such as improvement in a turnover rate of aged skin, amelioration of rough skin, and amelioration effect on keratin.

However, low-molecular-weight hyaluronic acid is poor in shapability, and therefore film formation with only low-molecular-weight hyaluronic acid has substantially been impossible. It is to be noted that it is possible to form a composite film even with low-molecular-weight hyaluronic acid by using it together with a natural polymer or synthetic polymer other than hyaluronic acid. However, there have been some cases where it cannot necessarily be said that the polymer material, which is used together with low-molecular-weight hyaluronic acid, is suitable in terms of antigenicity or biodegradability depending on the type of the polymer compound. Further, since low-molecular-weight hyaluronic acid is poor in shapability, there has also been a problem that it is difficult to increase the amount to be compounded.

The present invention has been completed in view of such problems of the conventional techniques, and an object of the present invention is to provide a cosmetic shaped product: which is substantially formed with relatively low-molecular-weight hyaluronic acid or a water-soluble salt thereof having a high penetrability into the skin; which is easily soluble to water; and which has satisfactory handling properties. Another object of the present invention is to provide a method for producing the cosmetic shaped product.

Solution to Problem

That is according to the present invention, a cosmetic shaped product described below is provided.

[1] A cosmetic shaped product being a sponge-like shaped body formed with at least one polyanionic polysaccharide of hyaluronic acid and a water-soluble salt thereof each having an average molecular weight of 30,000 or lower, the sponge-like shaped body having a bulk specific gravity of 5 to 500 mg/mL.

[2] The cosmetic shaped product according to [1], having a content of the polyanionic polysaccharide of 90% by mass or more.

[3] A felt-like cosmetic shaped product (hereinafter, also written as "felt-like shaped body") being a compressed product of the cosmetic shaped body according to [1] or [2].

[4] A fragmentary cosmetic shaped product (hereinafter, also written as "fragmentary shaped body") being a crushed product of the cosmetic shaped body according to [1] or [2].

In addition, according to the present invention, a method for producing a cosmetic shaped product, described below, is provided.

[5] A method for producing a cosmetic shaped product, the method being a method for producing the cosmetic shaped product according to [1] or [2], and comprising a step of freeze-drying an aqueous solution of the polyanionic polysaccharide, wherein a content of the polyanionic polysaccharide in the aqueous solution is 0.5 to 30% by mass.

Advantageous Effects of Invention

According to the present invention, a cosmetic shaped product: which is substantially formed with relatively low-molecular-weight hyaluronic acid or a water-soluble salt thereof having a high penetrability into the skin; which is easily soluble to water; and which has satisfactory handling properties can be provided. The cosmetic shaped product of the present invention is substantially formed with low-molecular-weight hyaluronic acid or the like which easily penetrates into the skin, and therefore effects of activating skin cells, improving a turnover rate of the aged skin, ameliorating rough skin, ameliorating keratin, and the like are expected. In addition, according to the present invention, a method for producing the above-described cosmetic shaped product can be provided.

BRIEF DESCRIPTION OF DRAWINGS

FIG. 1 is a photograph showing a polyethylene terephthalate tray used in Examples.

FIG. 2 includes photographs showing an aspect of a sponge-like shaped body (left-hand side) produced in Example 1 and an aspect of a felt-like shaped body (right-hand side) produced in Example 3.

FIG. 3 is a photograph showing an aspect of a fragmentary shaped body produced in Example 4.

FIG. 4 is a photograph showing an aspect of a film-like shaped body produced in Comparative Example 2.

DESCRIPTION OF EMBODIMENTS

Hereinafter, embodiments of the present invention will be described, but the present invention is not limited to the following embodiments.

Cosmetic Shaped Product

Sponge-Like Shaped Body

A cosmetic shaped product of the present invention is a sponge-like shaped body substantially formed with a polyanionic polysaccharide having an average molecular weight of 30,000 or lower. The polyanionic polysaccharide is at least any one of hyaluronic acid and a water-soluble salt of hyaluronic acid. The bulk specific gravity of this sponge-like shaped body is 5 to 500 mg/mL. Hereinafter, details on the cosmetic shaped product of the present invention will be described.

The polyanionic polysaccharide that forms the cosmetic shaped product of the present invention is at least any one of hyaluronic acid and a water-soluble salt of hyaluronic acid. Examples of the water-soluble salt of hyaluronic acid include an inorganic salt, an ammonium salt, and an organic amine salt of hyaluronic acid. Specific examples of the inorganic salt include: a salt of an alkali metal, such as sodium or potassium; an alkaline earth metal salt, such as a calcium salt; and a salt of a metal, such as zinc or iron.

The average molecular weight of commercially available hyaluronic acid and a water-soluble salt thereof is usually in a range of about several thousand to about 3000000. In contrast, the molecular weight of hyaluronic acid or a water-soluble salt thereof that constitutes the cosmetic shaped product of the present invention is relatively low. Specifically, the average molecular weight of hyaluronic acid or a water-soluble salt thereof that constitutes the cosmetic shaped product of the present invention is 30,000 or lower, preferably 20,000 or lower, and still more preferably 10,000 or lower. Such low-molecular-weight hyaluronic acid is excellent in penetrability into the skin, but, on the other hand, the shapability is not so satisfactory, as described previously. In contrast, the cosmetic shaped product of the present invention that can be produced by the method which will be described later is easily soluble to water and has satisfactory handling properties.

The "average molecular weight" of hyaluronic acid in the present specification means the "viscosity-average molecular weight" which is calculated from the intrinsic viscosity of a solution of hyaluronic acid. The viscosity-average molecular weight can be determined by a known measurement method. Specifically, hyaluronic acid or a water-soluble salt thereof (dried product) is dissolved in a 0.2 M sodium chloride solution to determine the intrinsic viscosity ($\eta$) at 30±0° C. with a Ubbelohde viscometer, and the viscosity-average molecular weight is calculated based on the Laurent equation ($\eta$ (intrinsic viscosity)=$3.6 \times 10^{-4} \cdot M^{0.78}$ (M: viscosity-average molecular weight). The intrinsic viscosity ($\eta$) is measured by Method I: Viscosity measurement by capillary tube viscometer of Viscosity Measurement, GENERAL TESTS in The Japanese Pharmacopoeia, Sixteenth Edition.

Hyaluronic acid extracted from a tissue such as a crest, a vitreous body of eyes of a cow, or the umbilical cord by an extraction method can be used. In addition, hyaluronic acid produced by a so-called fermentation process, in which hyaluronic acid is produced by culturing a microorganism that produces hyaluronic acid, can also be used. Hyaluronic acid that constitutes the cosmetic shaped product of the present invention may be hyaluronic acid produced by any one of the method and the process.

Commercially available hyaluronic acid and water-soluble salt thereof can be used in addition to hyaluronic acid and a water-soluble salt thereof each extracted or produced in-house. Specific examples of the commercially available hyaluronic acid and water-soluble salt thereof include trade name "Hyalo-Oligo" (manufactured by Kewpie Corporation, average molecular weight of 10,000 or lower), trade name "Micro Hyaluronic Acid FCH (manufactured by Kikkoman Corporation, average molecular weight of 5,000 or lower), and trade name "Hyalonano" (manufactured by Kewpie Corporation, average molecular weight of 2,000 or lower).

The cosmetic shaped product of the present invention is a sponge-like shaped body having a bulk specific gravity of 5 to 500 mg/mL, preferably 30 to 300 mg/mL. Because the cosmetic shaped product of the present invention is a sponge-like shaped body having a bulk specific gravity in the above-described range, the cosmetic shaped product of the present invention is quickly and easily soluble to water and has good handling properties. When the bulk specific gravity is less than 5 mg/mL, the hygroscopicity is easily made high, so that a sticky feeling occurs on the sponge-like shaped body, or deformation or the like occurs due to moisture absorption in some cases. On the other hand, when the bulk specific gravity exceeds 500 mg/mL, the rate of dissolution into water is lowered, so that an undissolved residue occurs easily. The "bulk specific gravity" of the cosmetic shaped product (sponge-like shaped body) in the present specification means "mass (mg) of sponge-like shaped body/apparent volume (mL) of sponge-like shaped body".

The cosmetic shaped product of the present invention is a sponge-like shaped body substantially formed with at least one polyanionic polysaccharide of hyaluronic acid and a water-soluble salt thereof. In the cosmetic shaped product of the present invention, the content of at least one polyanionic polysaccharide of hyaluronic acid and a water-soluble salt thereof is preferably 90% by mass or more, more preferably 92% by mass or more. It is to be noted that hyaluronic acid and a water-salt thereof has hygroscopicity, and therefore most of the balance is moisture, which unavoidably exists, in many cases. In addition, various additives and the like, which can be compounded in cosmetics and the like, may be contained in minute amounts as necessary as long as the effects of the present invention are not impaired.

Even though the cosmetic shaped product of the present invention is substantially formed with low-molecularweight hyaluronic acid, which is poor in shapability, the cosmetic shaped product of the present invention is a sponge-like shaped body having satisfactory handling properties. In addition, the cosmetic shaped product of the present invention quickly dissolves into water or lotion. For example, when the cosmetic shaped product of the present invention is stuck to the skin wetted with lotion, the cosmetic shaped product quickly dissolves on the stuck spot (on the skin) to be made into a high-concentration hyaluronic acid aqueous solution. Alternatively, adding an appropriate amount of water or lotion to the cosmetic shaped product can make a high-concentration hyaluronic acid aqueous solution. By applying and spreading this high-concentration hyaluronic acid solution with a fingertip, covering the vicinity of a desired spot (skin) with hyaluronic acid can be done. The cosmetic shaped product of the present invention is substantially formed with low-molecular-weight hyaluronic acid, which is an active ingredient, and has a high active ingredient concentration, and therefore effects such as retaining moisture, imparting a moist feeling, activating skin cells, improving a turnover rate of aged skin, ameliorating rough skin, and ameliorating keratin can be expected.

Felt-Like Shaped Body

By compressing the above-described sponge-like shaped body, a felt-like cosmetic shaped product (felt-like shaped body), which is a compressed product of the sponge-like shaped body, can be obtained. The method of compressing the sponge-like shaped body is not particularly limited, and the sponge-like shaped body may be compressed following an ordinary method. For example, by applying pressure to the sponge-like shaped body using a press machine or the like, a felt-like shaped body can be obtained.

Fragmentary Shaped Body

By crushing the above-described sponge-like shaped body, a fragmentary cosmetic shaped product (fragmentary shaped body), which is a crushed product of the sponge-like shaped body, can be obtained. The method of crushing the sponge-like shaped body is not particularly limited, and the sponge-like shaped body may be crushed following an ordinary method. For example, by using a blender, a mixer, or the like, and crushing the sponge-like shaped body with a rotary blade of these, a fragmentary shaped body can be obtained.

Both of the above-described felt-like shaped body and fragmentary shaped body have actions and effects which are equal to those of the sponge-like shaped body, which is a precursor for these shaped bodies, and therefore are each useful as a cosmetic shaped product.

Method for Producing Cosmetic Shaped Product

Next, a method for producing a cosmetic shaped product of the present invention will be described. The method for producing a cosmetic shaped product of the present invention includes a step (drying step) of freeze-drying an aqueous solution of at least one polyanionic polysaccharide of hyaluronic acid and a water-soluble salt thereof. The content of the polyanionic polysaccharide in the above-described aqueous solution to be freeze-dried is 0.5 to 30% by mass. Hereinafter, details on the method for producing a cosmetic shaped product of the present invention will be described.

In the drying step, the aqueous solution of the polyanionic polysaccharide is freeze-dried. The content (concentration) of the polyanionic polysaccharide in this aqueous solution is 0.5 to 30% by mass, preferably 2 to 25% by mass. High-molecular-weight hyaluronic acid is difficult to dissolve into water, so that there is a tendency that high-molecular-weight hyaluronic acid is easily made into a so-called lump state. On the other hand, low-molecular-weight hyaluronic acid for use in the present invention can be dissolved into water in a relatively easy manner. In addition, the aqueous solution of the low-molecular-weight polyanionic polysaccharide exhibits fluidity even though the concentration is relatively high, and therefore operations such as dispensing are easy to perform.

When the content of the polyanionic polysaccharide in the aqueous solution is less than 0.5% by mass, a large number of pores are formed in the sponge-like shaped body (cosmetic shaped product) which is obtained through freeze-drying, resulting in lowering the strength, so that keeping the shape is made difficult and handling is made difficult in some cases. On the other hand, when an attempt of preparing an aqueous solution having a content of the polyanionic polysaccharide exceeding 30% by mass is made, the polyanionic polysaccharide is liable to be left undissolved. By changing the content of the polyanionic polysaccharide in the aqueous solution, the porosity and bulk specific gravity of a resultant sponge-like shaped body (cosmetic shaped product) can be controlled.

The prepared aqueous solution of hyaluronic acid is poured into a suitable container, such as a tray. The material of the container is not particularly limited, and examples thereof include: polymer materials such as silicone, polypropylene, and polyethylene terephthalate; and materials made of a metal such as stainless steel and aluminum. Also, the shape of the container is not particularly limited, and a container adjusted to a desired shape/size of the cosmetic shaped products (manufactured goods), or a large-sized container in which a plurality of reservoirs (boxes) are formed can appropriately be used. In addition, a large-sized sponge-like shaped body produced using a large-sized container may be cut into a desired shape/size. By appropriately controlling the depth (height of a liquid layer) of the aqueous solution of hyaluronic acid, to be poured into the container, a sponge-like shaped body having a desired thickness can be obtained. Specifically, by making the depth about 0.5 to about 3 mm, a sponge-like shaped body that is easy to use as a cosmetic can be obtained.

From the viewpoints of safety, storability, and the like, it is preferable to minimize the number of unwanted bacteria in resultant cosmetic shaped products (manufactured goods). It is difficult to sterilize hyaluronic acid by heating, and therefore it is preferable to eliminate bacteria by, for example, filtrating the aqueous solution of hyaluronic acid with a filter of about 0.2 μm. In addition, it is preferable to minimize the number of unwanted bacteria in the production environment including the inside of a freezing tank and of a vacuum freeze dryer.

The aqueous solution of hyaluronic acid, poured into the container, is cooled and frozen (pre-freezing). Pre-freezing may be performed in a suitable freezing tank, or pre-freezing may be performed in a vacuum freeze dryer. When pre-freezing is performed in a vacuum freeze dryer, a series of processes from pre-freezing to freeze drying can be carried out continuously in a vacuum freeze dryer, and therefore contamination can be suppressed. The freezing temperature may be set to a temperature equal to or lower than the temperature at which the aqueous solution of hyaluronic acid freezes. When the concentration of hyaluronic acid is high, the aqueous solution of hyaluronic acid may be frozen at a lower temperature. Specifically, the freezing temperature is preferably set to −20° C. or lower, and is more preferably set to −40° C. or lower. In addition, to obtain a sponge-like shaped body in which uniform bubbles are formed, it is preferable to subject the aqueous solution to rapid freezing. Specifically, the cooling rate is preferably made faster than −1° C./min, and is still more preferably made faster than −4° C./min.

By freeze-drying the aqueous solution of hyaluronic acid following an ordinary method, a cosmetic shaped product, which is a sponge-like shaped body, can be obtained. The degree of vacuum may be set to about 0.05 Torr, and the shelf temperature may be set to about normal temperature to about 120° C. The time required for freeze-drying is not particularly limited, and the aqueous solution of hyaluronic acid may be dried until it can be ascertained that water has evaporated sufficiently. Specifically, the aqueous solution of hyaluronic acid is preferably dried until the water content becomes 15% by mass or less, and is still more preferably dried until the water content becomes 10% by mass or less in order to prevent adhesion between the sponge-like shaped bodies (manufactured goods) and deterioration in product quality.

EXAMPLES

Hereinafter, the present invention will be described specifically based on Examples, but the present invention is not limited to these Examples. It is to be noted that "parts" and "%" in Examples and Comparative Examples are each on a mass basis unless otherwise noted.

Production of Sponge-Like Shaped Body

Example 1

A powder of hyaluronic acid (trade name "Hyalo-Oligo", manufactured by Kewpie Corporation, average molecular weight of 10,000 or lower) was dissolved in distilled water to prepare a 5% hyaluronic acid aqueous solution. On the other hand, a polyethylene terephthalate tray, in which 80 boxes of 15 mm×15 mm×10 mm (volume of 2.25 mL) as shown in FIG. 1 were formed, was prepared. The prepared hyaluronic acid aqueous solution was dispensed in an amount of 1.5 mL in each box of the prepared tray. The tray was placed on a drying shelf of a vacuum freeze dryer (trade name "RLEII-103", manufactured by Kyowa Vacuum Engineering Co., Ltd.), and the drying shelf was cooled to −40° C. to freeze the hyaluronic acid aqueous solution. Thereafter, vacuum drying was performed at a degree of vacuum of 7.5×10$^{-2}$ Torr for 12 hours to obtain a sponge-like shaped body shown on the left-hand side of FIG. 2. The bulk specific gravity of the obtained sponge-like shaped body was 55 mg/mL. The water content of the sponge-like shaped body immediately after being taken out of the vacuum freeze dryer, as measured using an infrared moisture meter, was 7.4%.

Example 2

A sponge-like shaped body was obtained in the same manner as in Example 1 described previously, except that a 20% hyaluronic acid aqueous solution was prepared, and the prepared 20% hyaluronic acid aqueous solution was used. The bulk specific gravity of the obtained sponge-like shaped body was 233 mg/mL. The water content of the sponge-like shaped body immediately after being taken out of the vacuum freeze dryer, as measured using an infrared moisture meter, was 8.8%.

Comparative Example 1

A sponge-like shaped body was obtained in the same manner as in Example 1 described previously, except that a 0.1% hyaluronic acid aqueous solution was prepared, and the prepared 0.1% hyaluronic acid aqueous solution was used. However, a large number of pores were formed in the obtained sponge-like shaped body, so that the strength was remarkably lowered, and therefore it was extremely difficult to take a sponge-like shaped body out of a box of the tray with the shape of the sponge-like shaped body kept as it was. The bulk specific gravity of the obtained sponge-like shaped body was 1 mg/mL.

Comparative Example 2

The 5% hyaluronic acid aqueous solution prepared in Example 1 was poured into a stainless steel tray of 9 cm×12 cm in such a way that the height of the liquid surface was 6.7 mm (liquid amount: about 72 mL). The tray was placed in a fan dryer the temperature of which was adjusted to 20° C., thereby drying the solution to find that a cracked film as shown in FIG. 4 was formed. It was difficult to take the formed film out of the tray. In addition, when water was given to the film, some parts of the film were made into lump states and undissolved residues occurred.

Solubility Test

The sponge-like shaped bodies (about 12 mg each) obtained in Examples 1 and 2 were each put into a polypropylene test tube in which 20 ml of distilled water was placed to stir a resultant mixture for 15 seconds using a desk type mixer for a test tube. As a result, both of the sponge-like shaped bodies quickly dissolved. On the other hand, about 12 mg of the powder of hyaluronic acid, which was used as a raw material in producing the sponge-like shaped body of Example 1, was put into a polypropylene test tube in which 20 ml of distilled water was placed to stir a resultant mixture for 15 seconds using a desk type mixer for a test tube. As a result, some parts of the powder were made into lump states and undissolved residues occurred.

Production of Felt-Like Shaped Body

Example 3

Pressure was applied using a manual type press machine (trade name "VD-10", manufactured by ROMANOFF) to compress the sponge-like shaped body obtained in Example 1, and a felt-like shaped body shown on the right-hand side of FIG. 2 was thereby obtained. When water was given to the obtained felt-like shaped body, the obtained felt-like shaped body quickly dissolved.

Production of Fragmentary Shaped Body

Example 4

The sponge-like shaped body obtained in Example 1 was crushed using a handy blender (trade name "IFM-800", manufactured by Iwatani Corporation) to obtain a fragmentary shaped body shown in FIG. 3. When water was given to the obtained fragmentary shaped body, the obtained fragmentary shaped body quickly dissolved.

INDUSTRIAL APPLICABILITY

The cosmetic shaped product of the present invention is useful as a cosmetic to which effects of, for example, activating skin cells, improving a turnover rate of aged skin, ameliorating rough skin, ameliorating keratin, and the like are expected.

The invention claimed is:

1. A cosmetic shaped product, the product being a shaped body in a sponge form,
    wherein the shaped body is formed with at least one polyanionic polysaccharide selected from the group consisting of hyaluronic acid and a water-soluble salt thereof each having an average molecular weight of 30,000 or lower,
    the shaped body has a bulk specific gravity in a range from 5 to 500 mg/mL, and
    the cosmetic shaped product has a content of the polyanionic polysaccharide in a range of 90% by mass or more.

2. A cosmetic shaped product in a felt form, the product being a compressed product of the shaped body in a sponge form according to claim 1.

3. A method for producing the cosmetic shaped product according to claim 1, the method comprising:
    freeze-drying an aqueous solution of the polyanionic polysaccharide, wherein a content of the polyanionic polysaccharide in the aqueous solution is in a range from 0.5 to 30% by mass.

* * * * *